(12) United States Patent
Blenke et al.

(10) Patent No.: US 6,713,159 B1
(45) Date of Patent: Mar. 30, 2004

(54) TEAR-RESISTANT BOND PATTERN

(75) Inventors: Timothy James Blenke, Neenah, WI (US); Gregory Lynn Malchow, Oshkosh, WI (US); Daniel Hoo, Appleton, WI (US); Jeffry Jon Radke, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 329 days.

(21) Appl. No.: 09/651,042

(22) Filed: Aug. 30, 2000

(51) Int. Cl.[7] .............................................. B32B 27/12
(52) U.S. Cl. ...................... 428/195; 428/198; 442/394; 442/398
(58) Field of Search ............................... 428/195, 198; 442/394, 398; 604/372

(56) References Cited

U.S. PATENT DOCUMENTS

| 3,087,833 A | * | 4/1963 | Drelich ........................ 277/369 |
| 3,575,764 A | * | 4/1971 | McFarren ................. 156/306.6 |
| 4,275,105 A | * | 6/1981 | Boyd et al. .................. 428/198 |

FOREIGN PATENT DOCUMENTS

WO           99/14415          * 3/1999

* cited by examiner

Primary Examiner—Elizabeth M. Cole (74) Attorney, Agent, or Firm—Kimberly-Clark Worldwide (57) ABSTRACT

This invention pertains to bonded composites, and absorbent articles comprising such bonded composites. The bonded composites comprise first and second layers of thin-section sheet material bonded by bond elements defining a bond pattern. The bond pattern has a length, and width. The bond pattern includes a first sub-array of longitudinally-oriented separate and distinct stress receptor elements proximate the side edges, and spaced at first distances from each other, and a second sub-array of longitudinally-oriented separate and distinct transfer and dissipation elements preferably disposed inwardly of the side edges and inwardly of the stress receptor elements, and at second distances from the stress receptor elements less than spacing of the stress receptor elements from each other. Bonds can be activated by application of thermal or ultrasonic energy, or pressure e.g. against adhesive. The thin-section elements can comprise polymeric material selected from the group consisting of polyolefins, polyesters, and polyamides, and copolymers, mixtures, and blends of such polymeric materials, and are preferably structured as fibrous, film, or foam work pieces. The composite contact length at a given point along the length of the pattern preferably varies from the average composite contact length by no more than about 13 percent. In preferred embodiments, stress transfer and dissipation elements direct stresses inwardly into the interior of the pattern. In some embodiments, transfer and dissipation elements have first ends disposed on the interior of the pattern, and extend to second ends adjacent side edges of the pattern between respective ones of the stress receptor elements.

59 Claims, 5 Drawing Sheets

|    | A     | B     | C     | D     |
|----|-------|-------|-------|-------|
| 1  | 0.030 | 0.030 |       | 0.060 |
| 2  | 0.030 | 0.030 |       | 0.060 |
| 3  | 0.030 | 0.031 |       | 0.061 |
| 4  | 0.030 | 0.032 |       | 0.062 |
| 5  | 0.030 | 0.033 |       | 0.063 |
| 6  | 0.030 | 0.034 |       | 0.064 |
| 7  | 0.030 | 0.035 |       | 0.065 |
| 8  | 0.030 | 0.035 |       | 0.065 |
| 9  | 0.014 | 0.019 | 0.035 | 0.068 |
| 10 | 0.030 | 0.035 |       | 0.064 |
| 11 | 0.034 | 0.035 |       | 0.069 |
| 12 | 0.035 | 0.035 |       | 0.069 |
| 13 | 0.035 | 0.035 |       | 0.069 |
| 14 | 0.035 | 0.035 |       | 0.069 |
| 15 | 0.035 | 0.035 |       | 0.069 |
| 16 | 0.035 | 0.035 |       | 0.069 |
| 17 | 0.035 | 0.035 |       | 0.069 |
| 18 | 0.035 | 0.035 |       | 0.069 |
| 19 | 0.035 | 0.035 |       | 0.069 |
| 20 | 0.035 | 0.035 |       | 0.069 |
| 21 | 0.035 | 0.033 |       | 0.067 |
| 22 | 0.035 | 0.026 |       | 0.060 |
| 23 | 0.035 | 0.026 |       | 0.061 |
| 24 | 0.035 | 0.030 |       | 0.065 |
| 25 | 0.035 | 0.030 |       | 0.065 |
| 26 | 0.034 | 0.030 |       | 0.064 |
| 27 | 0.033 | 0.030 |       | 0.063 |
| 28 | 0.031 | 0.030 |       | 0.061 |
| 29 | 0.030 | 0.030 |       | 0.060 |
| 30 | 0.030 | 0.030 |       | 0.060 |
| 31 | 0.030 | 0.030 |       | 0.060 |
| 32 | 0.030 | 0.030 |       | 0.060 |
| 33 | 0.031 | 0.030 |       | 0.061 |
| 34 | 0.033 | 0.030 |       | 0.063 |
| 35 | 0.034 | 0.030 |       | 0.064 |
| 36 | 0.035 | 0.030 |       | 0.065 |
| 37 | 0.035 | 0.030 |       | 0.065 |
| 38 | 0.035 | 0.027 |       | 0.061 |
| 39 | 0.035 | 0.026 |       | 0.060 |
| 40 | 0.035 | 0.033 |       | 0.067 |
| 41 | 0.035 | 0.035 |       | 0.069 |
| 42 | 0.035 | 0.035 |       | 0.069 |
| 43 | 0.035 | 0.035 |       | 0.069 |
| 44 | 0.035 | 0.035 |       | 0.069 |
| 45 | 0.035 | 0.035 |       | 0.069 |
| 46 | 0.035 | 0.035 |       | 0.069 |
| 47 | 0.035 | 0.035 |       | 0.069 |
| 48 | 0.035 | 0.035 |       | 0.069 |
| 49 | 0.035 | 0.035 |       | 0.069 |
| 50 | 0.034 | 0.035 |       | 0.069 |
| 51 | 0.030 | 0.035 |       | 0.064 |
| 52 | 0.014 | 0.019 | 0.035 | 0.068 |
| 53 | 0.028 | 0.035 |       | 0.063 |
| 54 | 0.030 | 0.035 |       | 0.065 |
| 55 | 0.030 | 0.034 |       | 0.064 |
| 56 | 0.030 | 0.033 |       | 0.063 |
| 57 | 0.030 | 0.032 |       | 0.062 |
| 58 | 0.030 | 0.031 |       | 0.061 |
| 59 | 0.030 | 0.030 |       | 0.060 |
| 60 | 0.030 | 0.030 |       | 0.060 |
| 61 |       |       |       | 0.064 |

TEAR-RESISTANT BOND PATTERN

BACKGROUND

The present invention relates to a bonded composite of a first thin-section element of sheet material and a second thin-section element bonded together by bond elements defining a bond pattern. More particularly, one of the contemplated applications for the present invention is in bonding outer cover and body side liner thin-section elements of absorbent articles to one another.

Absorbent articles have been known for a long time as personal care hygiene products. Absorbent articles find use, for example, as diapers, training pants, incontinence products, women's sanitary pads, and the like. Such absorbent articles are designed and constructed to absorb and store liquid bodily excretions such as urine, menstrual fluid, or blood. Women's sanitary pads are used, for example, to absorb the liquids excreted prior to, during, and after menstruation.

In absorbent articles, the portions of the article where different layers or components are bonded to each other tend to incur significant stress concentrations and can be susceptible to fracture at such bonded locations. Conventional bond patterns position adjacent bond elements in uniform straight lines and crossing rows. The inventors herein have noted the tendency for the absorbent article to fracture at such bond locations, and for such fracture to proceed along the line defined by the respective side edge of the bond pattern. Conventional bond patterns operate somewhat like the tearing of paper forms along perforated lines of weakness.

The problem addressed by the present invention is twofold. The first aspect of the problem is to design a bond pattern which is process friendly by having a bond contact area at the bonding nip, which contact area in the nip is consistent over time. Such consistent bond contact area is controlled largely by the bonding lands of a roll participating in a bonding nip where such bonds are created, e.g. by ultrasonic frequency energy using a rotary ultrasonic horn, and corresponding anvil bearing the lands defining the respective bond pattern. Conventional bond patterns, having substantially greater variation in the bond contact area, develop excessive stresses in the bonding apparatus related to developing the bonds, and resulting from those variations, whereby useful life of such e.g. anvil roll is fore-shortened. In addition, the respective ultrasonic horn is unevenly worn due to variability of the bond pattern defined about the circumference of the anvil roll, or nonuniformity of the bond pattern, or a repeated "bumping," shock effect where the bond pattern does not provide for a relatively constant contact area between the bonding surface of the anvil roll and the bonding surface of the ultrasonic horn.

The second aspect of the problem is to provide a bonded composite demonstrating a bond pattern, and an absorbent article implementing the bond pattern, whereby the configuration of the bond pattern attenuates the tendency of the bonded composite or absorbent article to fracture along the bond pattern.

It is an object of this invention to reduce the tendency of bonded composites, or absorbent articles made therewith, to tear at the edge of the bond pattern, by incorporating into the bond pattern bond elements at locations and in configurations which attenuate fracture of the article, and which spread a concentrated stressing force over an increased area of the bonded composite or absorbent article.

It is another object of this invention to provide a relatively consistent bond contact width in the bonding nip, with respect to bonding apparatus, such that variations in the composite contact lengths of the bond elements, across the width of the bond pattern at any location along the length of the bond pattern, are 0.010 inch or less where the composite contact length is, for example, about 0.060 inch.

It is still another object of the invention to provide a relatively consistent bond contact width in the bonding nip, with respect to bonding apparatus, such that variations in the composite contact lengths of the bond elements are no more than 13 percent of the average composite contact length.

It is yet another object of this invention to provide a bond pattern which, when superimposed around the periphery of a horn or anvil roll, attenuates feedback spikes.

SUMMARY

This invention comprehends a first family of embodiments defining bonded composites, and absorbent articles comprising such bonded composites. Such bonded composite comprises as a first thin-section element, a first layer of thin-section sheet material. A second thin-section element is bonded to the first thin-section element by bond elements defining a bond pattern. The bond pattern has a pattern length, a pattern width represented by first and second side edges of the bond pattern, and a central longitudinal axis. The side edges of the bond pattern are defined generally by those areas of the respective thin-section elements which participate in absorbing and dissipating, by operation of the bond pattern, stresses received into the bond pattern. The bond pattern reflects application of force urging the first and second thin-section elements toward each other in face-to-face relationship to form an array of separate, distinct, and spaced elongate bond elements in a repeating arrangement affixing the first and second thin-section elements to each other. As ones of the bond elements, a first sub-array of longitudinally-oriented separate and distinct stress receptor elements is disposed proximate the side edges of the bond pattern, and spaced at first common distances from each other along the length of the bond pattern. As second ones of the bond elements, a second sub-array of longitudinally-oriented separate and distinct transfer and dissipation elements is disposed inwardly of the side edges and inwardly of the stress receptor elements, and at second distances from the stress receptor elements less than the spacing of respective ones of the stress receptor elements from each other.

In some embodiments, respective transfer and dissipation elements have first ends disposed on the interior portion of the bond pattern, and extend to second ends adjacent the side edges of the bond pattern between respective ones of the stress receptor elements. The stress transfer and dissipation elements thus direct stresses inwardly to the interior portion of the bond pattern, and dissipate such stresses at the interior portion of the bond pattern.

Bonds corresponding to the bond elements can be activated by application of e.g. thermal energy or ultrasonic-frequency energy to at least one of the first and second thin-section elements.

In preferred embodiments, at least one of the first and second thin-section elements comprises polymeric material selected from the group consisting of polyolefins including polyethylenes and polypropylenes, polyesters, and polyamides, and, copolymers, mixtures, and blends of such polymeric materials.

In preferred embodiments, structure of at least one of the first and second thin-section elements comprises a fibrous web defining a multiplicity of randomly-spaced small openings extending from a major surface of the web into the interior portion of the web.

In a second family of embodiments, ones of the transfer and dissipation elements extend across the width of the bond pattern, from loci proximate the side edges, at angles of about 10 degrees to about 65 degrees, preferably about 15 degrees to about 50 degrees, more preferably about 20 degrees to about 40 degrees, and optionally about 30 degrees, with respect to the longitudinal axis. A bond width is defined by the width of the pattern perpendicular to the longitudinal axis, including spaces between bond elements, at any point along the length of the pattern. The bond width extends a long the pattern width. Bond element contact lengths are correspondingly defined a long the bond width. The combination of the bond element contact lengths along a respective bond width defines a composite contact length for the respective bond width. The composite contact length, taken at equally spaced intervals along the length of the bond pattern, defines an average composite contact length along the length of the bond pattern. Each composite contact length at a given point along the length of the bond pattern varies from the average composite contact length by no more than about 13 percent, preferably no more than about 10 percent, and more preferably no more than about 8 percent.

In some embodiments of this family, the bond pattern comprises, as first ones of the bond elements, a first sub-array of longitudinally-oriented separate, distinct, and spaced stress receptor elements disposed along the length of the bond pattern, proximate the side edges of the bond pattern and, as second ones of the bond elements, a second sub-array of longitudinally-oriented separate, distinct, and spaced transfer and dissipation elements disposed along the length of the bond pattern, inwardly of the side edges and, correspondingly, generally inwardly of the stress receptor elements. Respective ones of the transfer and dissipation elements have spaced first and second ends, and legs extending from the respective ends toward each other and outwardly of the longitudinal axis along the length of the bond pattern to outwardly-disposed portions of the legs disposed between the stress receptor elements.

In preferred embodiments, the stress receptor elements alternate along the length, and on opposing side edges, of the bond pattern. An imaginary contact line spanning the width of the bond pattern at a given locus along the length of the bond pattern intersects a stress receptor element on a given side of the bond pattern, and also intersects, on the opposing side of the bond pattern, an outwardly-disposed portion of a respective leg of a corresponding transfer and dissipation element. In combination, the distance between distal ends of the most remote ones of the bond elements along a respective imaginary line spanning the width of the bond pattern so defined represents at least about 70 percent, preferably at least about 80 percent, more preferably at least about 85 percent, of the width of the bond pattern. The distance between distal ends of the most remote ones of the bond elements along a respective imaginary line spanning the width of the bond pattern so defined can comprise as much as 90 percent, or 95 percent, and up to 100 percent of the width of the bond pattern. As a result, outwardly-disposed portions of the legs provide balancing support on opposing sides of the longitudinal axis from respective stress receptor elements or legs of respective transfer and dissipation elements, during formation of the bond pattern.

In some embodiments, ones of the transfer and dissipation elements extend from loci proximate the side edges up to loci proximate the longitudinal axis.

In some embodiments, increases and decreases in power distribution across the width of the bond pattern can be defined by variations in composite contact lengths as compared to the average composite contact length for a given bond pattern for at least a complete circumferential rotation of a rotary anvil. Variations in composite contact lengths of the bond pattern reflect no more than about 13% of the average composite contact length of the bond pattern throughout the complete circumferential anvil rotation.

In a third family of embodiments, respective transfer and dissipation elements have spaced first and second ends, and legs extending from the respective first and second ends toward each other and outwardly of the longitudinal axis along the length of the bond pattern to outwardly-disposed portions of the legs, joined to each other, between the stress receptor elements. Such stress transfer and dissipation elements direct stresses inwardly into the interior of the bond pattern.

In preferred embodiments, the first and second ends of the transfer and dissipation elements dissipate the stresses primarily on the interior of the bond pattern.

In other embodiments, ones of the transfer and dissipation elements extend from loci proximate the side edges up to loci proximate the longitudinal axis.

In a fourth family of embodiments, respective transfer and dissipation elements have first ends disposed on the interior of the bond pattern, the respective transfer and dissipation elements extending to second ends adjacent the side edges of the bond pattern between respective ones of the stress receptor elements.

In a fifth family of embodiments, a steady power distribution across the width of the bond pattern defines minimum variations in composite contact lengths as compared to the average composite contact length for the bond pattern for at least a complete circumferential rotation of a rotary anvil reflecting the bond pattern, wherein variations in composite contact lengths of the bond pattern reflect no more than about 13 percent of the average composite contact length of the bond pattern throughout the complete circumferential anvil rotation.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustra-

DESCRIPTION OF THE ILLUSTRATED EMBODIMENTS

Figure 1A:
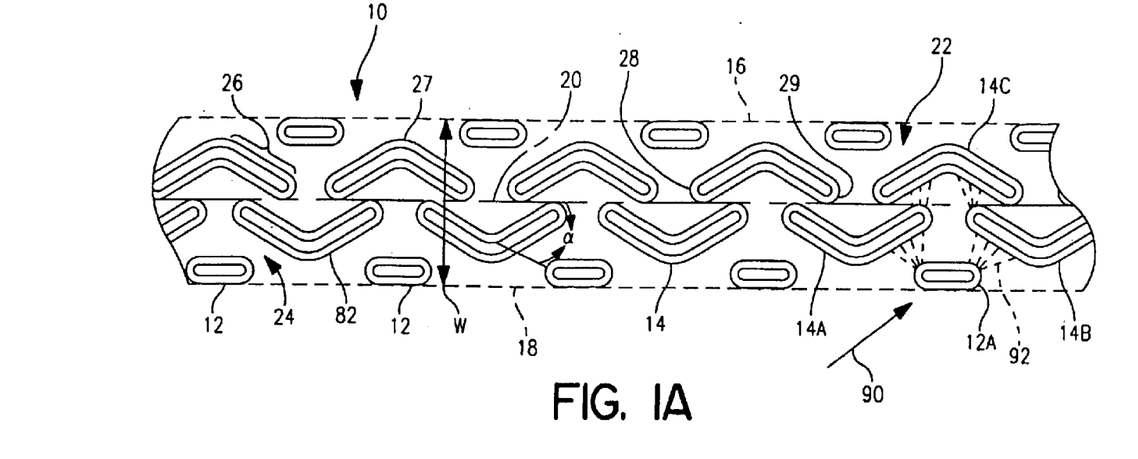
FIGS. 1A and 1B show plan views of representative bond patterns of this invention.

FIG. 1A shows a bond pattern 10 having a first side edge 16, a second side edge 18, and a central longitudinal axis 20 which divides the bond pattern 10 into a first opposing pattern combination 22 on a first side of axis 20 and a second opposing pattern combination 24 on an opposing 'second side of axis 20. Bond pattern 10 has a pattern length defined in terms of distance measured along central longitudinal axis 20, and a pattern width "W" represented by distance between first side edge 16 and second side edge 18 of bond pattern 10. Correspondingly, the overall area of bond pattern 10 is defined as the area which participates in absorbing and dissipating, by operation of the bond pattern 10, stresses received into the bond pattern 10 from external sources, and is generally defined within the confines of side edges 16 and 18.

The bond pattern reflects application of force which urges first and second thin-section elements toward each other in face-to-face relationship to form, as repeating bond segments, an array of separate, distinct, and spaced elongate bond elements in a repeating arrangement affixing the first and second thin-section elements to each other. Ones of the bond elements extend width-wise across the bond pattern, from loci proximate the side edges up to at least about the longitudinal axis, at angles "α" of between about 10 degrees and about 65 degrees, preferably about 15 degrees to about 50 degrees, with respect to the longitudinal axis. Most preferred angles are about 25 degrees to about 40 degrees. The angles illustrated in the drawings represent about 30 degrees from the longitudinal axis.

While legs 26 are shown in the drawings as being straight, the legs can be curved in some embodiments. In such case, the respective angles "α" vary along the lengths of such legs in accord with the respective curvatures of the legs.

A bond width is defined by an end-to-end length corresponding to bond elements arrayed across the width of the pattern perpendicular to the longitudinal axis, including spaces between respective ones of the bond elements, and spaces between bond elements and side edges 16, 18. A bond width can be measured at any point along the length of the bond pattern, and such bond width extends along the pattern width. The bond width thus corresponds to the pattern width "W" at a given locus along the length of the bond pattern.

Bond element contact lengths at respective bond elements are correspondingly defined along the bond width. The additive combination of the bond element contact lengths along a respective bond width defines the composite contact length along the respective bond width. The composite contact length, taken at equally spaced intervals along a length of the bond pattern, defines an average composite contact length. The composite contact length at a given point along the length of the pattern varies from the average composite contact length by no more than about 13 percent, preferably by no more than about 10 percent, and more preferably by no more than about 8 percent.

In the illustrated embodiments, opposing pattern combinations 22 and 24 are substantially the same and are employed as off-set mirror images of each other. Thus, pattern combinations 22, 24 are positioned along the length of the pattern such that the opposing pattern combinations are asymmetric with respect to each other by expression of such offset. While the opposing patterns are asymmetric with respect to each other, both first opposing pattern combination 22 and second opposing pattern ii combination 24 are internally symmetric, as well as expressing repeating segments thereof along the length of bond pattern 10.

Bond pattern 10 is defined by a plurality of bond elements. In preferred embodiments, bond elements proximate side edges 16, 18 are spaced farther apart from each other than bond elements which are disposed more away from the side edges, thus creating a pattern density which is less dense at the side edges of the pattern than away from the side edges.

Bond pattern 10 preferably comprises regularly repeating bond segments, each repeating bond segment comprising a defined set of bond elements spaced according to a generally fixed segment pattern. A plurality of bond elements establishing repeated element combinations defines such bond segment, although not all bond elements need be defined in bond segments. Therefore, a similar bond pattern using one or more orphan bond elements which orphan elements do not repeat regularly, or which elements are so far outside the rest of the bond pattern that such bond elements do not cooperatively participate with the other bond elements in absorbing and dissipating, by operation of the bond pattern, stresses received into the bond pattern, is within the scope of the present invention.

The illustrated bond pattern comprises, as a first sub-array of the bond elements, longitudinally-oriented separate, distinct, and spaced stress receptor elements 12 disposed at or near, namely proximate, first side edge 16 and second side edge 18. Receptor elements 12 are typically evenly spaced along the length of bond pattern 10.

Stress transfer and dissipation elements 14 define a second sub-array of longitudinally-oriented separate, distinct, and spaced bond pattern elements, typically evenly spaced along the length of bond pattern 10, inwardly of the side edges of the bond pattern and generally inwardly of stress receptor elements 12. Each respective transfer and dissipation element has a first end 28 and a second end 29, and legs 26 extending from the respective ends toward each other and outwardly of the longitudinal axis, and meeting at an outwardly-disposed joiner locus 27 of the legs 26 between stress receptor elements 12. Stress receptor elements 12 alternate along the length, and on opposing side edges, of the bond pattern. Stress transfer and dissipation elements 14 alternate on opposing sides, and along the length, of bond pattern 10, generally between respective stress receptor elements. Stress transfer and dissipation elements 14 thereby provide the desired side-to-side balance to the bond element width of bond pattern 10.

In general, then, preferred bond patterns comprises regularly repeating bond segments, each repeating bond segment comprising at least one stress receptor element 12 and at least one respective stress transfer and dissipation element 14, the elements 12 and 14 being spaced according to a generally fixed segment pattern wherein each stress receptor element 12 is balanced by a transfer and dissipation element, or a stress termination element, or both, or other balancing element or elements, on the opposing side of longitudinal axis 20.

Figure 4:
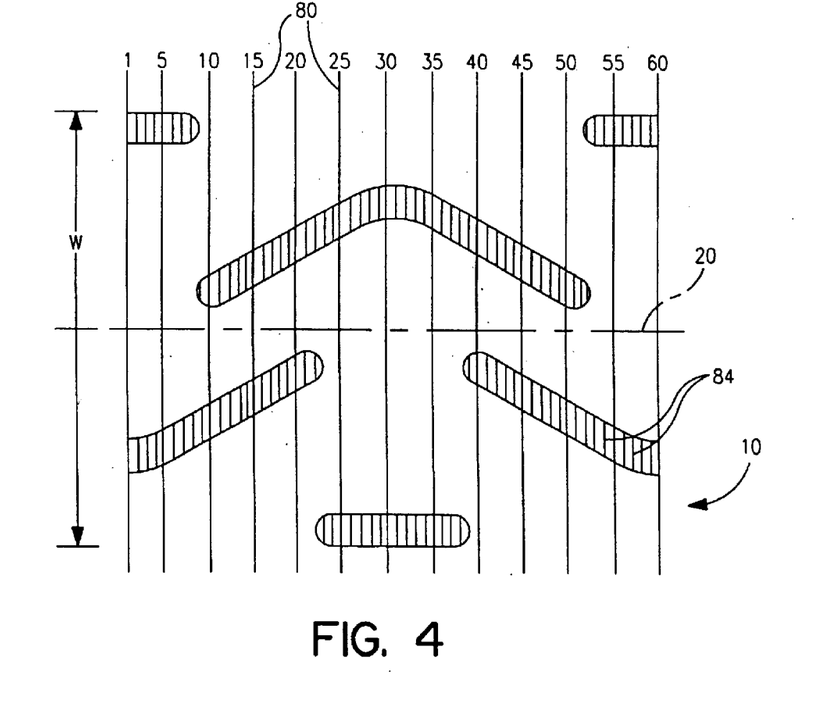
FIG. 4 shows an enlarged view the of bond pattern and the relationship between imaginary connection lines and respective bond elements.

In e.g. the embodiments illustrated in FIG. 1A, an imaginary line 80, shown in FIG. 4, along a given bond width at a given locus along the length of the bond pattern traverses a stress receptor element 12 on a first side of longitudinal axis 20 and a preferably outwardly-disposed portion of a respective leg 26 of the corresponding transfer and dissipation element 14 on the opposing side of the axis. The distance between distal ends of the most remote ones of the bond elements along a respective imaginary line spanning the width of the bond pattern, so defined and illustrated in FIG. 4, represents at least about 70 percent, up to 100 percent, of the width of the bond pattern, more preferably, at least about 75 percent up to about 90 percent, of the width of the bond pattern, and even more preferably at least about 80 percent up to about 85 percent, of the width of the bond pattern.

The distance between the ends of the composite contact length is illustrated as less than 100 percent of the width of the bond pattern, wherein the transfer and dissipation elements are located inwardly of side edges 16, 18. In some embodiments, the outer portions 82 of the transfer and dissipation elements can be disposed at side edges 16, 18, whereby the composite contact length can be as great as 100 percent of the width of the bond pattern at the given locus along the length of the web.

Thus, outwardly-disposed portions of respective legs 26 of the transfer and dissipation elements provide balancing support on opposing sides of the longitudinal axis balancing e.g. respective stress receptor elements 12 during formation of the bond pattern 10.

Because stress transfer and dissipation elements 14 extend both directions along the length of the bond pattern, elements 14 can transfer, to the interior of the bond pattern, stresses coming from either direction along the length of the bond pattern. Similarly, angles "α" of the transfer and dissipation elements 14 tend to promote the transfer of stresses to the interior of the bond pattern, and are effective to transfer stresses entering the bond pattern from any direction inwardly from the side edges and toward the interior of the bond pattern. Additionally, because of the similarity of the opposing pattern combinations located on opposing sides of central longitudinal axis 20, the bond pattern effectively balances nip force exerted on one side of the pattern with a balancing nip force on the opposing side of the bond pattern, while the bonds are being formed.

Figure 1B:
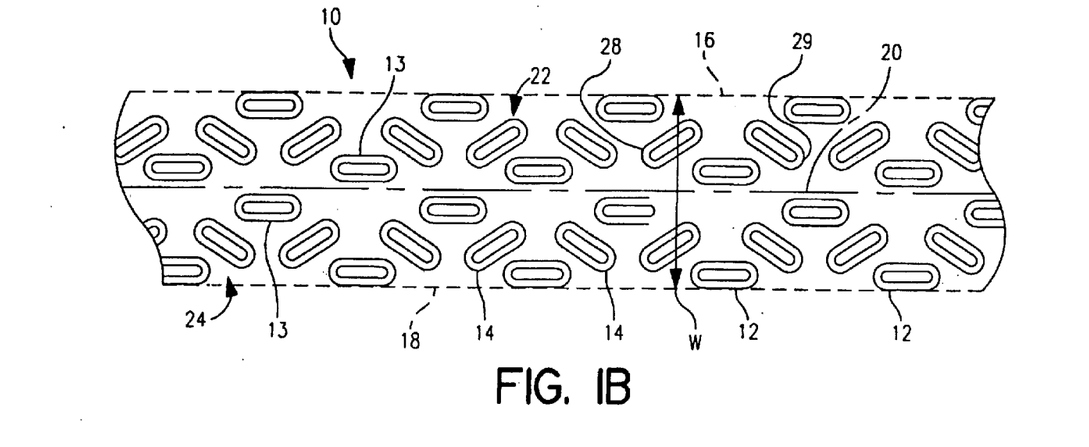

In an embodiment illustrated by FIG. 1B, and starting with the structure of FIG. 1A, portions of the stress transfer and dissipation elements where the legs join 27 in FIG. 1A have been excised and reinserted at or near the central longitudinal axis 20 and on the same side of the pattern as the respective donor transfer and dissipation element, thus to provide respective stress termination elements 13. Stress termination elements 13 tend to coordinate degeneration, dissipation, and preferably termination, of stresses transferred into the interior portion of the bond pattern adjacent axis 20.

The resilience of materials known for use in e.g. the body side liner or the outer cover of absorbent articles, in combination with controlled pattern density, enables the bond pattern to direct inwardly toward the longitudinal axis a wide variety of forces imposed on the bond pattern from any direction along the length or width of the bond pattern. By directing, transferring, and distributing stresses toward the interior of the bond pattern, the invention relieves a corresponding portion of the stress which is typically borne by side edge portions of the bond pattern. Thus, the stress born by the respective side edge when a given force is imposed on the bond pattern, is less for bond patterns of the invention than for a conventional bond pattern having a symmetrically arrayed square pattern of lines and rows of circular bond elements. Accordingly, bond patterns of the invention can tolerate more overall stress than such conventional bond patterns. Thus, not only does the bond pattern reduce the straight-line, perforation-like tendency of conventional linearly-arranged bond patterns, but the invention is correspondingly capable of tolerating and distributing greater levels of stress than a conventional pattern.

Bond pattern 10 can be used to unite sheets of material along the entirety of the length of the material, or as in the case of the examples cited, along a portion of the length or width of a personal care absorbent article. Bond pattern 10 can also be used to unite intermittent portions of respective work pieces in a particular configuration e.g. defined in terms of length and/or width. Bond pattern 10 can further be used to unite portions of work pieces according to more than one configuration. Bond pattern 10 can yet further be used to unite materials along a defined length of web material. In all such implementations, bond pattern 10 can be used to bond a relatively smaller element or work piece to a relatively larger element or work piece. Examples for use of the bond pattern in an absorbent article include, but are not limited to, bonding a fastening ear to the outer cover, bonding a leg flap to the outer cover or the body side liner, bonding containment flaps to the body side liner, and bonding a landing zone to the outer cover.

In yet another embodiment, bond pattern 10 comprises a pattern density defined generally by the number of bond elements within a defined portion of the pattern area, wherein bond elements proximate the side edges are spaced farther apart from each other than bond elements which are disposed more away from the side edges, thus creating a pattern density which is less dense at the side edges of the pattern than away from the side edges.

Figure 2:
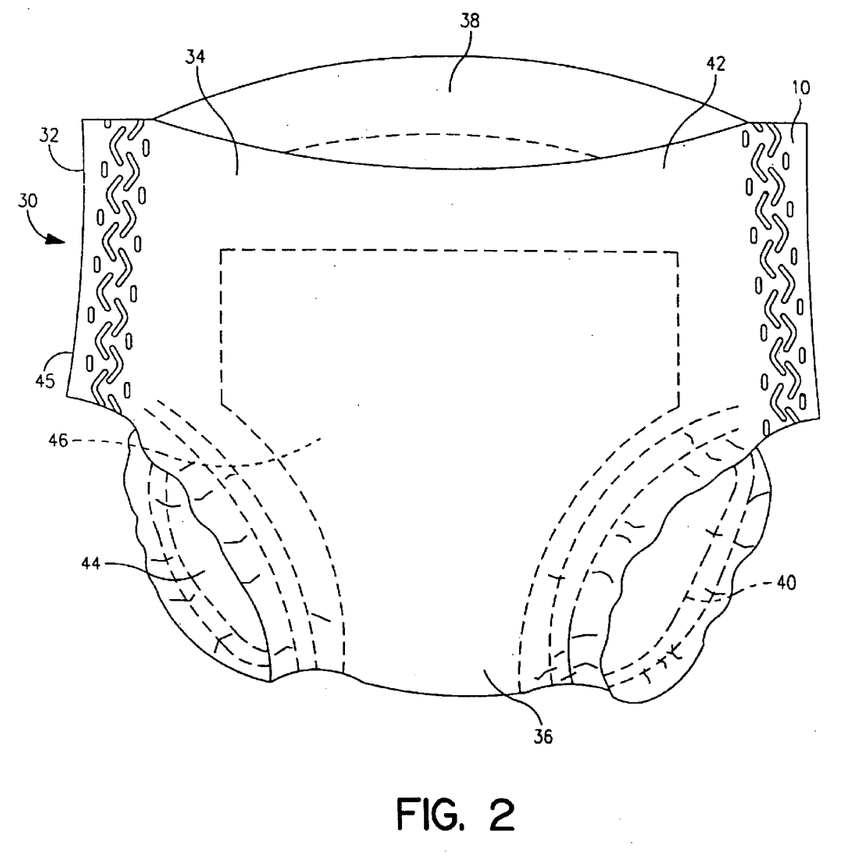
FIG. 2 shows, as a representative absorbent article, a pair of training pants illustrating use of the bond pattern of FIG. 1 along the side seams.

Referring to FIG. 2, an exemplary absorbent article, namely a pair of training pants 30, illustrates the use of bond pattern 10 of FIG. 1A. In FIG. 2, the training pants have a front portion 34, a rear portion 38, and a crotch portion 36 which extends from front portion 34 to rear portion 38. The absorbent article of FIG. 2 comprises a liquid-impermeable outer first thin-section element of sheet material as outer cover 42, a liquid-permeable body side second thin-section element as body side liner 44, and a liquid-absorbent core 46 disposed between the outer cover and the body side liner. Side seams 32 employ the illustrated bond pattern 10 to join the front and rear portions at side edges 45. Leg elastics 40 extend along leg openings 49.

Various woven and nonwoven fabrics may be used in fabricating body side liner 44. For example, body side liner 44 can be fabricated using a perforated or reticulated film, or a meltblown or spunbonded web of polymeric material selected from the group consisting of polyolefins including polyethylenes and polypropylenes. polyesters, and polyamides, and mixtures, copolymers, and blends of such polymeric fibers. The body side liner can also comprise, alone or in combination, a carded and/or bonded web composed of natural and/or synthetic fibers. Body side liner 44 can also be composed of a substantially hydrophobic material wherein the hydrophobic material is treated with a surfactant or otherwise processed to impart a desired level of wettability and hydrophilicity.

Body side liner 44 can comprise, for example, a nonwoven, spunbonded, polypropylene fabric employing about 2.8–3.2 denier fibers formed into a web having a basis weight of about 22 grams per square meter and a density of about 0.06 grams per cubic centimeter. The fabric is then surface treated with about 0.3 weight percent of a suitable surfactant. Body side liner 44 can also be fabricated employing a fibrous web defining a multiplicity of randomly-spaced small openings extending from a major surface of the web into the interior of the web. The body side liner 44 can comprise material structure such as porous foams, reticulated foams, apertured polymeric films, polymeric fibers, and natural fibers. The body side liner can be defined in terms of length, width, and/or thickness by a multiplicity of components or layers which correspond with any of the materials disclosed herein, as well as others known in the art.

It is generally preferred that outer cover 42 of the absorbent article be formed from material which is substantially impermeable to liquids. A typical outer cover can be manufactured from a thin plastic film or other flexible liquid-impermeable material. For example, the outer cover can be formed from a film of polymeric material selected from the group consisting of polyolefins including polyethylenes and polypropylenes, polyesters, and polyamides, and mixtures, copolymers, and blends of such polymeric materials, the resulting outer cover having a thickness, for example, of from about 0.012 millimeter to about 0.051 millimeter. If outer cover 42 should have a more cloth-like feeling, the outer cover can comprise a polyethylene film laminated to a surface of a nonwoven web, such as a spunbonded web of polyolefin fibers. For example, a polyethylene film having a thickness of about 0.015 millimeter can have thermally or otherwise laminated thereto a spunbonded web of polyolefin fibers having thicknesses of from 1.5 to 2.5 denier per filament, which nonwoven web has a basis weight of about 24 grams per square meter. Further, outer cover 42 can be formed of a woven or nonwoven fibrous web which has been totally or partially constructed or treated to impart a desired level of liquid impermeability to selected regions which are adjacent or proximate absorbent core 46. Still further, the outer first thin-section element 42 can optionally be composed of a micro-porous material which permits vapors to escape from absorbent core 46, through outer cover 42 and into the ambient environment, while preventing liquid exudates from passing through the outer cover.

One or both of the outer cover and the body side liner can comprise a fibrous web defining a multiplicity of randomly-spaced small openings extending from a major surface of the web into the interior of the web. Polymeric material selected from the group consisting of polyolefins including polyethylenes and polypropylenes, polyesters, and polyamides, and mixtures, copolymers, and blends of such polymeric materials can be used, in either film form, solid or reticulated, or in non-woven fiber forms, for one or both of body side liner 44 and outer cover 42. Also, included in definitions of the above polymeric materials are all routine, common, and normal additives known to those skilled in the art of polymeric materials, such as for example and without limitation, processing aids, chemical stabilizers, compatibilizers where more than one polymer is used, and fillers.

Absorbent core 46 suitably comprises a matrix of hydrophilic fibers, such as a web of cellulosic fluff, in combination with a high-absorbency material commonly known as superabsorbent material. Absorbent core 46 can comprise a mixture of superabsorbent hydrogel-forming particles and wood pulp fluff. In place of the wood pulp fluff, one can use synthetic polymeric e.g. meltblown fibers or a combination of synthetic fibers and natural fibers. The superabsorbent material can be substantially homogeneously mixed with the hydrophilic fibers or can be otherwise combined into absorbent core 46.

Alternatively, absorbent core 46 can comprise a laminate of fibrous webs, optionally UCTAD, and superabsorbent material or other suitable means of maintaining a superabsorbent material in a localized area.

Absorbent core 46 can have any of a number of shapes. For example, absorbent core 46 can be rectangular, I-shaped or T-shaped. It is generally preferred that absorbent core 46 be narrower in the crotch portion than in the rear portion or the front portion of the absorbent article to the extent the absorbent article includes a waist portion, which waist portion typically has a greater width than the width at the crotch portion.

The high-absorbency material in absorbent core 46 can be selected from natural, synthetic or modified natural polymers and materials. The high absorbency material can be inorganic material, such as silica gels, or organic compounds such as polymers, e.g. cross-linked polymers. "Superabsorbents," which are optionally cross-linked materials, as referred to herein, refers to any means for effectively rendering normally water-soluble materials substantially water insoluble but swellable, whereby absorbent properties are available but the swelled material is substantially immobile after absorbing water-based liquids. Such means can include, for example and without limitation, physical entanglement, crystalline domains, covalent bonds, ionic complexes and associations, hydrophilic associations such as hydrogen bonding, and hydrophobic associations or Van der Waals forces.

In embodiments of the invention indicative of an absorbent article as e.g. illustrated in FIG. 2, the width of the bond pattern between the first and second side edges of the bond pattern is preferably about 4 millimeters to about 20 millimeters, and more preferably about 5 millimeters to about 14 millimeters. In some contemplated embodiments of the invention, the width of the bond pattern may even be up to about 4 inches.

The greater the width of the bond pattern, the more material can be included in the stress attenuation process, but the more material is used and, for a fixed number of bond elements, the greater the risk that the stress can pass through the bond pattern without being terminated. Thus, if the element-to-pattern-area ratio is too low, the elements are unable to cooperatively support each other whereby the stress may not be adequately attenuated in the bond pattern and whereby a lack of minimum bond element density may result in layers of a bonded composite disassociating with one another. Conversely, the less the width of the bond pattern, the less material is used, but the greater the risk of not effectively spreading the stress away from the entry loci at the respective side edge. Thus, selection of a preferred specific width is a judgement to be made based on the technical features present in a given set of circumstances, including consideration of the principles of the invention.

Figure 3:
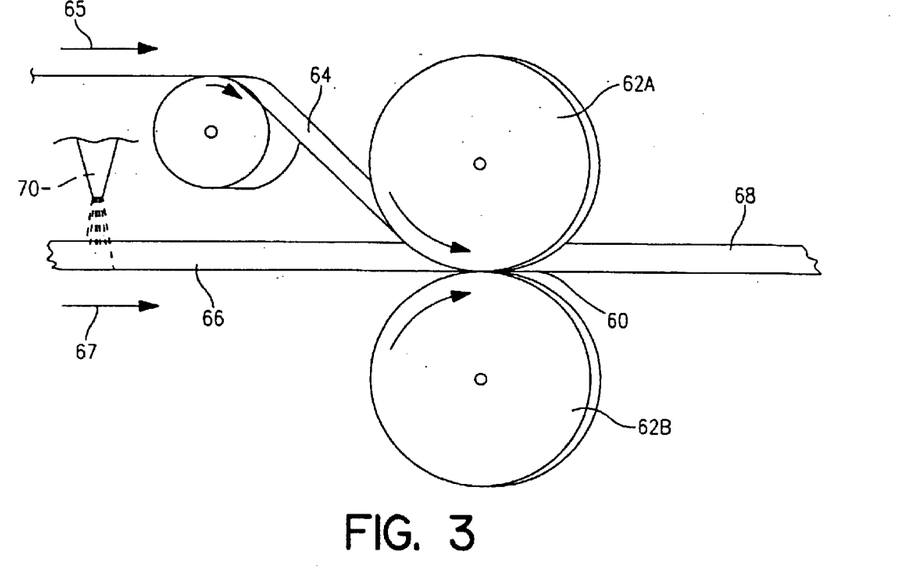
FIG. 3 shows a representative pictorial side elevation of a bonding nip such as can be used in continuous bonding processes employing bond patterns of the invention.

FIG. 3 represents a side pictorial view of bonding nip 60 such as can be used in continuous bonding processes employing bond patterns of the invention. Bonding nip 60 is formed between two rotating rolls 62A. 62B. Rolls 62A. 62B can be mounted at any angular orientation, each with respect to the other, so long as energy can be effectively transmitted from at least one of the rolls to the material being worked in nip 60. In FIG. 3, rolls 62A. 62B are mounted such that roll 62A is positioned vertically over roll roll 62B. To create the bond pattern of the invention, a first web of sheet material 64 and a second web of sheet material 66 are fed from left to right in FIG. 3 as indicated by arrows 67, 69, and are urged toward each other in face-to-face relationship, in the bonding nip 60 of the machine shown in FIG. 3, to form an array of separate, distinct, and spaced elongate bond elements affixing the first and second thin-section sheet materials to each other.

The bond elements described herein and illustrated in the drawings are formed by, among other steps, pressing e.g.

webs 64 and 66 against each other in nip 60 in order to activate a desired form of adhesion. Typically, one of the rolls, e.g. roll 62A, has a generally smooth outer circumferential surface while the other roll, e.g. roll 62B, bears a pattern of raised bonding protrusions, also called lands, corresponding in design and location to the bond pattern reflected in FIGS. 1, 2, and 4. While the outer surface of e.g. roll 62A can bear indentations complementing the protrusions, such is not preferred. As webs 64, 66 pass through the nip, rolls 62A, 62B in combination apply pressure to the webs at locations on the webs corresponding to the respective protrusions, thereby activating the adhesive response at e.g. bond elements 12 and 14.

The protrusions, which are shaped like respective bond elements, extend from a base surface on the outer circumference of roll 62B. The protrusions terminate at distal land surfaces which are responsible for creating the respective bond elements. Typical such protrusions can be, for example, up to approximately 0.10 inch in height, and up to about 0.06 inch in width. Height is defined as the dimension of the protrusion from the base circumferential surface of the roll to the distal tip, or land, which actually interfaces with e.g. the web material in which bonds are being formed. The sides of the protrusions typically extend from the base circumferential surface of the roll at angles of, for example, about 5 degrees to about 60 degrees, more preferably, about 10 degrees to about 50 degrees, to an angle perpendicular to the base circumferential surface at the respective locus on the surface of the anvil roll.

The bond pattern, as well as the individual bond elements, can be activated by a variety of methods including but not limited to applying pressure, thermal energy and pressure, or ultrasonic-frequency energy and pressure, to the workpiece in bonding nip 60. The workpiece defined for this illustration can include one or more of web 64, web 66, and the resultant bonded composite 68. Where ultrasonic energy is employed, the e.g. anvil roll 62B is properly sized, as known in the art, to not deleteriously interfere with the resonant frequency of the ultrasonic horn.

As an alternative to thermal energy or ultrasonic energy, adhesives can be used to create the bond pattern. FIG. 3 indicates an optional use of adhesive. While optional adhesive applicator 70 shows the adhesive being applied as a spray, optional adhesive applicator 70 is meant, in addition, to represent various other methods of applying adhesive, including but not limited to coating from a coating roll, dip coating, wire rod coating, and the like.

The types of adhesive contemplated for use in this invention include a wide range of known adhesives which are suitable for bonding the materials of interest, for example and without limitation, contact adhesives, pressure sensitive adhesives, hot melt adhesives, and two-part chemically activated adhesives.

In the embodiment illustrated in e.g. FIGS. 2 and 3, the bond pattern created by the process described and illustrated in FIG. 3 joins the superposed webs at locations generally corresponding to the ultimate locations of side seams 32 in the finished absorbent article. As stated previously, such articles typically comprise an assemblage of two or more layers or partial layers of different materials or can comprise two or more layers of substantially the same material, optionally along with other elements. Typical such material is a woven or non-woven fabric, or a polymer film.

As illustrated in FIG. 2, an absorbent article precursor, commonly referred to in the art as a work piece, can be defined as part of a continuously processed, continuous length, composite web of materials. As a work piece is defined, a bond pattern can be formed e.g. at side seams 32 either before or after the absorbent article is severed from the web, either as a fully finished or partially finished absorbent article.

While FIG. 3 shows only one method of implementing the bond pattern to form a bonded composite, other processes are contemplated such as creating the bond pattern using a plunge or press horn, or any other process capable of creating the bond pattern using e.g. pressure, thermal energy, ultrasonic energy, or adhesive. Additionally, the materials listed as possible materials capable of comprising an outer cover and a body side liner, as described in connection with FIG. 2, are exemplary and preferred materials for use in fabricating useful products according to the invention.

FIG. 4 shows an enlarged view of the bond pattern illustrated in FIGS. 1A and 2. FIG. 4 includes imaginary connection lines 80 spaced evenly along the length of bond pattern 10, to help illustrate the relationships between the respective bond elements and the cooperative effect of such spacial relationships as the positioning of the respective bond elements works to increase the wear life of both lower-disposed e.g. anvil roll 62B (FIG. 3) and upper-disposed roll 62A.

FIG. 4 represents a single repetition of the bond pattern illustrated in multiple repetitions in FIGS. 1 and 2, and along the length of the bond pattern. In FIG. 4, the several bond elements are shown divided by equally spaced imaginary increment lines 84 which extend perpendicular to longitudinal axis 10, and parallel to lines 80. In FIG. 4, each fifth line 84 is aligned with one of the lines 80. Thus, each fifth line 84 represents incremental portions of the length of a corresponding one of imaginary lines 80.

Lines 80 are used as convenient tools for indexing and evaluating the significance of lines 84. The spacing between respective lines 84, and the frequency of lines 80, can be selected as convenient for the user's analysis. In the illustrated embodiment, the distances between adjacent imaginary increment lines 84 are approximately 0.008 inch. Such distances are preferably uniform along the length of the pattern being evaluated. The length of the imaginary increment lines 84 generally represents at least the width "W" of the bond pattern. Each such distance defines one of the five increments used in defining a corresponding imaginary line 80. The illustrated bond pattern is designed to keep the composite contact length, which is indicative of the sum of the lengths of respective line segments of any one line 84 defined by each respective bond element crossed by any one line 84, including all sections thereof, within 0.010 inch of the average composite contact length. The illustrated pattern is also designed so that those projections or lands which are collective in forming the nip have combined widths, which define the composite contact length, which are relatively consistent, as measured along successive adjacent lines 84, over the full length of the segment, and wherein successive segments are both internally consistent within themselves, and are consistent with respect to each other.

Figure 5:
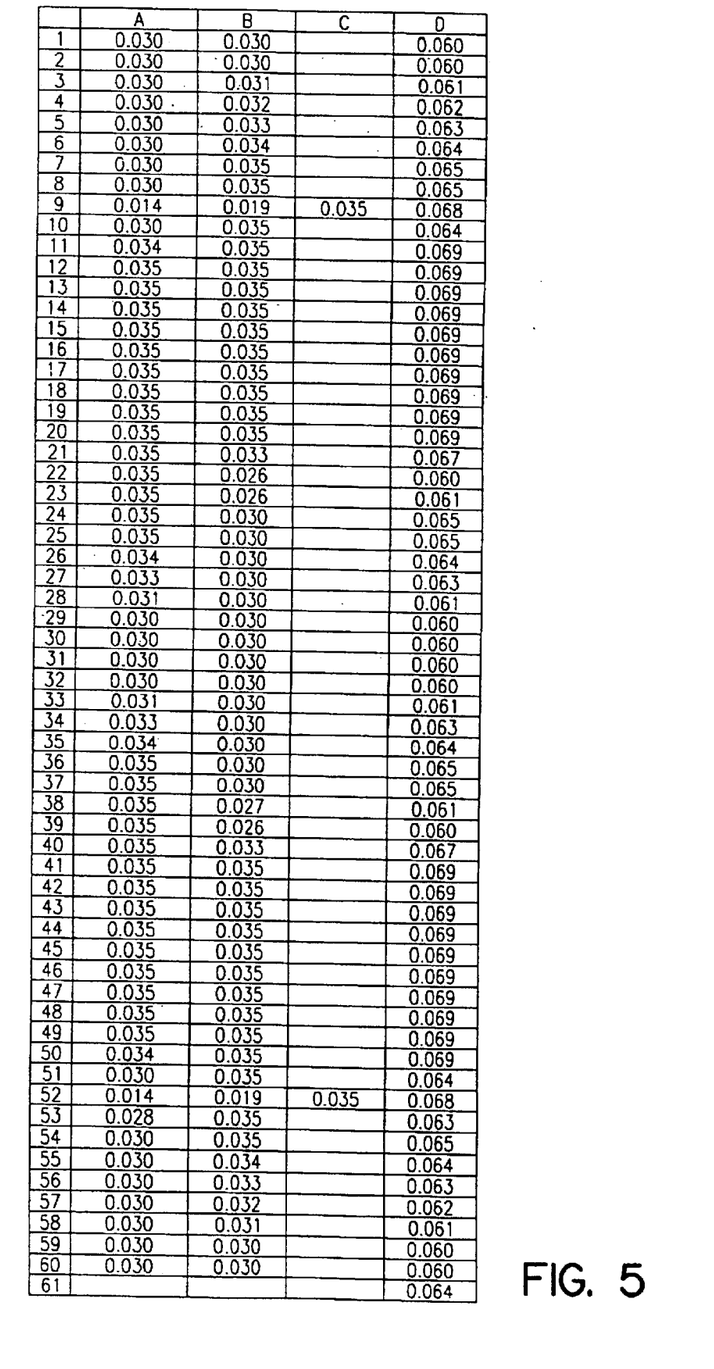
FIG. 5 is a table showing composite contact lengths of the bond elements across the width of the bond pattern, at spaced locations along the length of the bond pattern.
Figure 6:
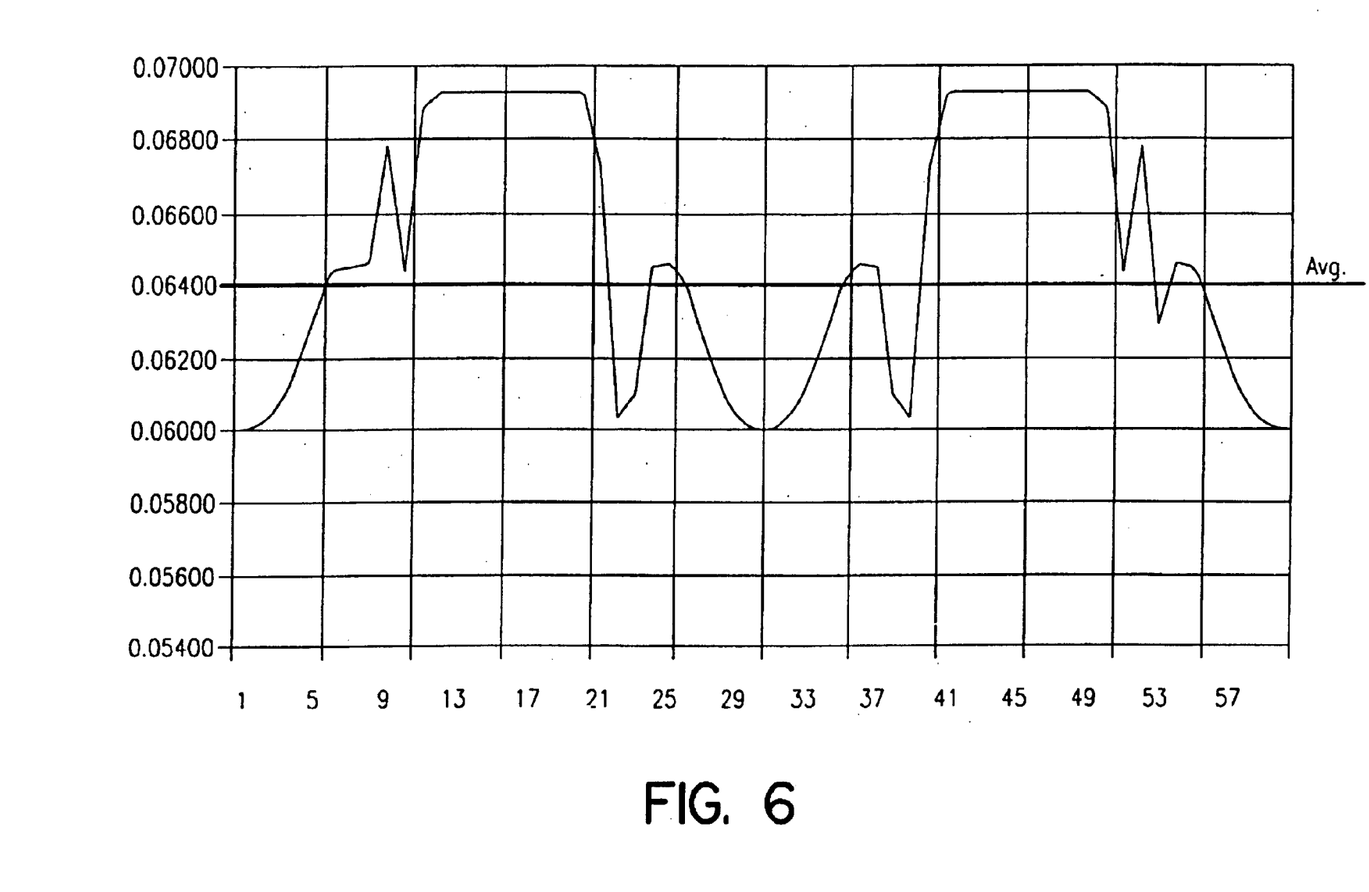
FIG. 6 shows a graph of the respective spaced locations illustrated in the table of FIG. 5.

Referring to FIGS. 5 and 6, a significant benefit of the present invention is attenuation of power feedback spikes in ultrasonic bonding embodiments of the invention in combination with consistency of bonding effect both longitudinally along the length of the bond pattern and laterally across the width of the bond pattern. Feedback spikes occur as a result of characteristics of contact variation in conventional bond patterns between e.g. a rotary anvil and a rotary ultrasonic horn. As used herein "power" represents a function of rotation of a rotary anvil combined with forces emitted from one or both the horn and anvil. The emitted forces can be any forces e.g. selected from the group consisting of pressure, ultrasonic energy, and thermal energy. Increases and decreases in power distribution across the width of a bond pattern can be defined by variations in composite contact lengths as compared to the average composite contact length for a given bond pattern for at least a complete circumferential rotation of an anvil.

Conventional bond patterns tend to demonstrate a wide variation in composite contact lengths as compared to respective average composite contact lengths. A variation in composite contact lengths causes a corresponding, and typically proportional, variation in power distribution for a conventional bond pattern. Such variation is a result of e.g. bond patterns defining a rectangular arrangement of rows and lines, perpendicular to each other, of points extending along and perpendicularly across the length of the bond pattern. Thus, composite contact length of such conventional pattern varies for each transverse row of points from a maximum contact length when the row is in the nip, to zero, or something approaching zero, between rows, thereby developing corresponding power spike extremes at each row of points/dots/circles, whereby the effective diameter of such anvil roll varies slightly between successive transverse rows of points, and wherein each such variation contributes to vibration of the horn and anvil at the nip.

The current invention demonstrates a variation in composite contact length of no more than about 13% from the average composite contact length as the respective anvil makes a complete rotation. The consistency in power distribution of the current invention, demonstrated by the lack of variance from the average composite contact length, degree of consistency of composite contact length, can also be indicative of consistency of resistance between the horn and the anvil, as contact area in the nip is a function of the respective composite contact lengths. Thus, minimum variation of respective composite contact lengths from the average composite contact length, as in the current invention, results In a steady power distribution across the width of the bond pattern and a consistent, predictable mechanical feedback that can be interpreted by suitable instrumentation.

In addition, the side-to-side balance of the pattern and the consistency of the composite contact length provide two further benefits. First, bending stress is attenuated on shafts supporting rolls 62A. 62B. Second, side-to-side surface wear on especially roll 62A is relatively more uniform, providing longer roll life than patterns not exhibiting such consistency of composite contact length.

Referring to FIG. 4, the composite contact length is defined as the sum of the line lengths along the widths of the bond elements traversed by a given imaginary increment line 84 between side edges 16 and 18. In the illustrated embodiment, imaginary increment lines are typically about 0.030 inch long on respective bond elements as shown in FIG. 5, and the overall pattern width "W" is about 0.380 inch. In such illustrated environment, variation in the composite contact length should be within 0.010 inch of the average composite contact length of the segment.

FIG. 5 is a table listing the individual linear lengths of the individual line sections 84, each representing separate and distinct bond elements in Columns A, B, and C for the lines 84 at the given numbered locations 1–60. The sum of the lengths shown in Columns A. B. C is shown as Column D, which represents the composite contact length of the respective collection of segments of a given increment line 84. The average composite contact length is 0.064 inch, with maximum of 0.069 inch and minimum of 0.060 inch. FIG. 5 illustrates a maximum deviation from average of −6.4 percent to +7.8 percent. This close tolerance makes for a relatively smoother running machine by having a relatively consistent land width for the cooperative working of rolls 62A. 62B in nip 60. As shown in Column "D" of FIG. 5, the bond pattern provides a consistent composite bond element width so that the variation of the composite contact length from average, at any point along the length of the bond segment, is 0.01 inch or less. FIG. 6 depicts a graph of the composite contact lengths of FIG. 5. The variation in FIGS. 5 and 6 is thus +7.8 percent to −6.3 percent. Some benefits of the invention are obtained where the variation is as great as plus or minus 13 percent. Preferred variations are plus or minus 10 percent. Target variations are plus or minus 8 percent, as only nominal benefit is achieved by reducing the variation to substantially less than 8 percent.

Returning to FIG. 4, an important value in bond patterns of the invention is that, during formation of the bond elements in the webs and/or work pieces, the loci of bonding contact in the nip is consistently represented by bond elements on both sides of longitudinal axis 20. For example, at any time a receptor element 12 is receiving pressure in the nip, a transfer and dissipation element 14 on the opposing side of axis 20 is also receiving pressure in the nip. Thus, any force on a supporting roll shaft arising from receptor element 12 is countered by a second force arising from the opposing transfer and dissipation element 14 and tending to balance the first force. FIGS. 4 and 5 illustrate such analyses for each of the 60 line combinations 84 represented in FIG. 4.

In addition to the reduction in shaft stress, such balanced pattern on anvil roll 62B provides for balanced wear across the width of the working surface of roll 62A. Such improved wear is especially valuable in an ultrasonic horn 62A when the bonds are formed using an ultrasonic bonding process. Indeed, the improved surface wear benefits are more apparent where rolls 62A. 62B have different base diameters. In ultrasonic bonding processes, anvil roll 62B typically is designed to have a diameter different from that of the ultrasonic horn so as to not unacceptably attenuate resonance of the horn. Additionally, an anvil having a different diameter than the horn provides for alleviating compatibility between the horn and anvil, thereby avoiding increased wear as a result of the same portions of the horn interacting with the same portions of the anvil. Such common occurrence of different roll diameters makes the bond patterns of the Invention, balanced as in FIGS. 4–6, especially valuable in ultrasonic bonding processes.

To that end, the pattern is suitably balanced, side to side, where the distance between distal ends of the most remote ones of the bond elements along a respective imaginary line spanning the width of the bond pattern so defined represents at least 70 percent as great as the width "W" of the bond pattern at the respective segment. Preferred distance is about 80 percent to 85 percent of width "W." The distance may be as great as 100 percent where e.g. bond elements 14 extend to the side edges of the bond pattern. However, some such embodiments may be subject to stress transfer along the side edges, whereby the design of such bond patterns must consider how stresses can be transferred toward the interior of the bond pattern, and away from the side edge, as taught herein.

A particular feature of bond pattern 10 is that of receiving stressing forces at stress receptor elements 12 proximate side edges 16, 18 and transferring such forces away from the respective side edge into the interior of the bond pattern.

Referring to FIG. 1, a stressing force 90 received at receptor element 12A is transmitted from receptor element 12A at the loci of smallest radius on the side of the receptor element opposite the stress receiving side. Dashed lines 92 illustrate the paths along which the stress traverses, away from receptor element 12A to transfer and dissipation elements 14A, 14B. The received stresses are similarly transmitted to the opposing sides of elements 14A, 14B, and thence outwardly from the smallest radius portions to element 14C. The above paths of transmission of the force into the interior of the bond pattern are indicated as paths 92 in FIG. 1. The indicated paths are merely illustrative, and not limiting, of the distribution of forces in bond patterns of the invention. However, such illustration is instructive that bond patterns of the invention, given the angles "α" and the spacing between receptor elements 12, actively direct'stresses into the interior of the bond pattern wherein a plurality of bond elements simultaneously absorb portions of the stress such that no one or two bond elements at the side edge of the bond pattern bear the entire burden of the stressing force. In the example of force 90, the stress is illustrated as being borne by four bond elements, three of which are larger in size than the receiving element 12, and thus can theoretically tolerate greater amounts of stress than can receptor element 12A.

In summary, a bond pattern of the invention operates as a compilation of different functioning elements of the pattern. The side edges, and thus the unit area, of the bond pattern are defined generally by those areas of the respective thin-section elements being bonded which participate in absorbing and dissipating, by operation of the bond pattern, stresses received into the bond pattern.

As stress is applied to a bonded composite or absorbent article demonstrating a bond pattern of the invention, stress is initially received at the side edge of the bond pattern by a stress receptor element 12 and is typically transferred to the next closest bond element, namely one or more transfer and dissipation elements. By designing the bond pattern so that the next closest bond element is located inwardly on the bond pattern, the stress is transferred inwardly of the bond pattern and away from the respective side edge, whereby the amount of stress dissipated, absorbed at the side edge is lessened by the amount of stress which is transferred inwardly into the bond pattern. By disposing elements 14 at angle "α" with the longitudinal axis, the stress travels inwardly not only in being transferred from bond element to bond element, but also in traveling along the length of bond elements 14 toward the inner ends of such elements.

To the extent the resultant stress is reduced at the side edge, by transfer inwardly from the side edge, the side edge may have unused stress-accepting capacity, whereby the bond patterns of the invention have increased stress-bearing capacity compared to otherwise similar and conventional bond patterns.

The increased stress-bearing capacity of bond patterns of the invention is attributable to the cooperative relationships among the respective bond elements. Stress receptor elements 12 initially receive stresses and relay the stresses inwardly to the next closest bond element in the pattern, for example an element 14. Stress transfer and dissipation elements 14 direct stresses inwardly further into the interior portion of the bond pattern, and the stresses are dissipated in the interior portion of the bond pattern.

Thus, assuming the tear strength of the material being bonded is not exceeded, bond patterns of this invention provide increased tear-resistance in a bonded composite, e.g. a bonded absorbent article, as compared to conventional bond patterns, by providing greater distances between adjacent bond locations for the pattern periphery, where the force-generated stress on the bond pattern is the highest. At the same time, the pattern is also conducive to maintaining the structural integrity of a rotary horn and anvil system by providing a relatively constant surface area contact, and side-to-side contact balance, between the horn and anvil.

While this invention has been described in terms of elongate bond elements, a limited number of circular bond elements can be used in the bond pattern so long as the number and placement of such circular bond elements are consistent with the principles taught herein for directing stress inwardly away from the side edges of the bond pattern.

Bond patterns of the invention typically comprise bond density of about 15 percent to about 50 percent, more preferably about 20 percent to about 40 percent. As used herein, "bond density" refers to the fraction of the bond area which is occupied by bond elements, e.g. stress receptor elements 12, stress transfer and dissipation elements 14, and/or stress termination elements 13. Such spacing of the bond elements from each other provides for distribution of stresses across unbonded portions of the bond pattern to a plurality of bond elements, thereby to enhance distribution of the stress over a relatively larger number of bond elements, as well as over a relatively larger area of the material being bonded. Such increased distribution of the stress operates to reduce the level of stress borne by a localized area of the bond pattern, thus reducing the maximum stress response intensity experienced by the bonded materials.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

What is claimed is:

1. A bonded composite, comprising:
   (a) a first flexible sheet material having first and second opposing major surfaces, the first and second major surfaces defining a first overall area of said first flexible sheet material, and a first web interior between the first and second major surfaces, said first flexible sheet material being suitable for use in a personal care absorbent article;
   (b) a second flexible sheet material having third and fourth opposing major surfaces, the third and fourth major surfaces defining a second overall area of said second flexible sheet material, and a second web interior between the third and fourth major surfaces, said second flexible sheet material being suitable for use in a personal care absorbent article, and being bonded to the first flexible sheet material by bond elements defining an elongate bond pattern, the elongate bond pattern having regularly repeating bond segments along a length thereof, the bond elements in each bond segment being spaced from each other according to a pattern of bond elements common to the respective bond segments, the bond pattern having a pattern length, and first and second side edges, the pattern length and the side edges, in combination, defining a third area within which the bond pattern is defined, the third area being smaller than at least one of the first and second areas of the respective first and second flexible sheet materials such that a portion of at least one of the first and second areas of respective said first and second flexible sheet materials is outside the bond pattern, the bond pattern having a bond pattern interior between the first and second side edges, and a pattern width between the first and second side edges, and a central longitudinal axis, the bond pattern comprising an array of separate, distinct, and spaced elongate bond elements in a repeating arrangement affixing said first and second flexible sheet materials to each other, ones of said bond elements extending across the width of said bond pattern, from loci proximate the side edges, at angles of between about 10 degrees and about 85 degrees with respect to the longitudinal axis, a bond width being defined by a distance between the first and second side edges perpendicular to the longitudinal axis, including spaces between bond elements, at any point along the length of the pattern, such bond width extending along the pattern width, bond element contact lengths being correspondingly defined along the bond width, the composite of the bond element contact lengths along a respective bond width defining a composite contact length for the respective bond width, the composite contact length, taken at equally spaced intervals along the length of the bond pattern, defining an average composite contact length, the composite contact length at a given point along the length of the pattern varying from the average composite contact length by no more than about 13 percent.

2. A bonded composite as in claim 1, the composite bond element contact length, at any point along the length of the pattern, varying from the average composite bond element contact length by no more than about 10 percent.

3. A bonded composite as in claim 1, the composite bond element contact length, at any point along the length of the pattern, varying from the average composite bond element contact length by no more than about 8 percent.

4. A bonded composite as in claim 1, said bond pattern comprising (i) as first ones of said bond elements, a first sub-array of longitudinally-oriented seperate, distinct, and spaced bond elements disposed along the length of the bond pattern, proximate the side edges of the bond pattern, and (ii) as second ones of said bond elements, a second sub-array of longitudinally-oriented separate, distinct, and spaced bond elements disposed along the length of the bond pattern, inwardly of the side edges of the bond pattern and generally inwardly of said first sub-array of bond elements, respective ones of said second sub-array of bond elements having spaced first and second ends, and legs extending from the respective ends toward each other and outwardly of the longitudinal axis along the length of the bond pattern to outwardly-disposed portions of said legs between respective ones of said first sub-array of bond elements.

5. A bonded composite as in claim 4, said first sub-array of bond elements alternating along the length, and on opposing side edges, of the bond pattern, an imaginary contact line spanning the width of the bond pattern at a given locus along the length of the bond pattern which intersects a said one of the bond elements of said first sub-array of bond elements on a given side of the bond pattern, also including, on the opposing side of the bond pattern, a said outwardly-disposed portion of a respective said leg of the corresponding one of the bond elements of said second sub-array of bond elements, such that the distance between distal ends of the most remote ones of the bond elements along the respective imaginary contact line spanning the width of the bond pattern represents at least about 70 percent, up to 40 percent, of the width of the bond pattern, whereby the outwardly-disposed portions of the respective said legs provide balancing support on opposing sides of the longitudinal axis from respective one of the bond elements of said first sub-array of bond elements or opposing one of the bond elements of said second sub-array of bond elements during formation of the bond pattern.

6. A bonded composite as in claim 4, said first sub-array of bond elements alternating along the length, and on opposing side edges, of the bond pattern, an imaginary contact line spanning the width of the bond pattern at a given locus along the length of the bond pattern which intersects a said one of the bond elements of said first sub-array of bond elements on a given side of the bond pattern, also including on the opposing side of the bond pattern, a said outwardly-disposed portion of a respective said leg of the corresponding bond element of said second sub-array of bond elements, such that the distance between distal ends of the most remote ones of the bond elements along the respective imaginary contact line spanning the width of the bond pattern represents at least about 75 percent, up to 90 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

7. A bonded composite as in claim 4, said first sub-array of bond elements alternating along the length, and on opposing side edges, of the bond pattern, an imaginary contact line spanning the width of the bond pattern at a given locus along the length of the bond pattern which intersects a said one of the bond elements of said first sub-array of bond elements on a given side of the bond pattern, also including on the opposing side of the bond pattern, a said outwardly-disposed portion of a respective said leg of the corresponding bond element of said second sub-array of bond elements, such that the distance between distal ends of the most remote ones of the bond elements along the respective imaginary contact line spanning the width of the bond pattern represents at least about 80 percent, up to 85 percent, of the width of the bond pattern, whereby the outwardly-disposed portions of the respective said legs provide balancing support on opposing sides of the longitudinal axis from respective ones of said bond elements of said first sub-array of bond elements or opposing ones of said bond elements of said second sub-array of bond elements during formation of the bond pattern.

8. A bonded composite as in claim 1 wherein bonds corresponding to said bond elements are formed by application of thermal energy to at least one of said first and second flexible sheet materials.

9. A bonded composite as in claim 1 wherein bonds corresponding to said bond elements are formed by application of ultrasonic-frequency energy to at least one of said first and second flexible sheet materials.

10. A bonded composite as in claim 1 wherein at least one of said first and said second flexible sheet materials comprises polymeric material select from the group consisting of polyolefins, polyesters, and polyamides, and copolymers, mixtures, and blends of said polymeric materials.

11. A bonded composite as in claim 1 wherein at least one of said first and said second flexible sheet materials comprises a fibrous web having a multiplicity of randomly-spaced small openings extending from one of the respective major surfaces into the interior of the respective web.

12. A bonded composite as in claim 1 wherein ones of said bond elements of said second sub-array of bond elements extend from loci proximate the side edges to loci proximate the longitudinal axis.

13. A bonded composite as in claim 1 wherein increases and decreases in power distribution across the width of the bond pattern, as the bond pattern is being formed, define variations in composite contact lengths as compared to the average composite contact length for a given bond pattern for at least a complete circumferential rotation of a rotary anvil, wherein variations in composite contact lengths of the bond pattern reflect no more than about 13 percent of the average composite contact length of the bond pattern throughout the complete circumferential anvil rotation.

14. A bonded composite, comprising:
(a) a first flexible sheet material having first and second opposing major surfaces, the first and second major surfaces defining a first overall area of said first flexible sheet material, and a first web interior between the first and second major surfaces, said first flexible sheet material being suitable for use in a personal care absorbent article;
(b) a second flexible sheet material having third and fourth opposing major surfaces, the third and fourth major surfaces defining a second overall area of said second flexible sheet material, and a second web interior between the third and fourth major surfaces, said second flexible sheet material being suitable for use in a personal cars absorbent article; and
(c) a multiplicity of bond elements defining bonds bonding said first and second flexible sheet materials to each other in a bond pattern, the bond pattern having a pattern length, and first and second side edges, the pattern length and the side edges, in combination, defining a third area within which the bond pattern is defined, the third area being smaller than at least one of the first and second areas of the respective first and second flexible sheet materials such that a portion of at least one of the first and second areas of respective said first and second flexible sheet materials is outside the bond pattern, the bond pattern having a bond pattern interior between the first and second side edges, and a pattern width between the first and second side edges, and a central longitudinal axis, the bond pattern comprising an array of separate, distinct, and spaced elongate bond elements in a repeating arrangement affixing said first and second flexible sheet materials to each other,
(d) as ones of said bond elements, a first sub-array of longitudinally-oriented separate and distinct bond elements disposed along the length, and proximate the side edges of, the bond pattern, the side edges of the bond pattern being defined generally between outwardly-disposed sides of sequentially-adjacent ones of said first sub-array of bond elements, and
(e) as ones of said bond elements, a second sub-array of longitudinally-oriented separate, distinct, and spaced bond elements disposed along the length of the bond pattern, inwardly of the side edges of the bond pattern and generally inwardly of said first sub-array of bond elements, respective ones of said second sub-array of bond elements having spaced first and second ends, and legs extending from the respective first and second ends toward each other and outwardly of the longitudinal axis along the length of the bond pattern to outwardly-disposed portions of said legs, joined to each other, between said ones of said first sub-array of bond elements.

15. A bonded composite as in claim 14, said ones of said first sub-array of bond elements alternating along the length, and on opposing side edges, of the bond pattern, an imaginary contact line spanning the width of the bond pattern at a given locus along the length of the bond pattern which intersects a said one of said first sub-array of bond elements on a given side of the bond pattern, also including on the opposing side of the bond pattern, a said outwardly-disposed portion of a respective said leg of the corresponding one of sand second sub-array of bond elements, such that the distance between distal ends of the most remote ones of the bond elements along the respective imaginary contact line spanning the width of the bond pattern represents at least about 70 percent, up to 100 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

16. A bonded composite as in claim 14, said ones of said first sub-array of bond elements alternating along the length, and on opposing side edges, of the bond pattern, an imaginary contact line spanning the width of the bond pattern at a given locus along the length of the bond pattern which intersects a said one of said first sub-array of bond elements on a given side of the bond pattern, also including on the opposing side of the bond pattern, a said outward disposed portion of a respective said leg of the corresponding one of said second sub-array of bond elements, such that the distance between distal ends of the most remote ones of the bond elements along the respective imaginary contact line spanning the width of the bond pattern represents at least about 75 percent, up to 90 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

17. A bonded composite as in claim 14, said ones of said first sub-array of bond elements alternating along the length, and on opposing side edges, of the bond pattern, an imaginary contact line spanning the width of the bond pattern at a given locus along the length of the bond pattern which intersects a said one of said first sub-array of bond elements on a given side of the bond pattern, also including on the opposing side of the bond pattern, a said outwards disposed portion of a respective said leg of the corresponding one of said second sub-array of bond elements, such that the distance between distal ends of the most remote ones of the bond elements along the respective imaginary contact line spanning the width of the bond pattern represents at least about 80 percent, up to 85 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

18. A bonded composite as in claim 14 wherein bonds corresponding to said bond elements are formed by application of thermal energy to at least one of said first and second flexible sheet materials.

19. A bonded composite as in claim 14 wherein bonds corresponding to said bond elements are formed by application of ultrasonic-frequency energy to at least one of said first and second flexible sheet materials.

20. A bonded composite as in claim 14 wherein at least one of said first and said second flexible sheet materials comprises polymeric material selected from the group consisting of polyolefins, polyesters, and polyamides, and copolymers, mixtures, and blends of said polymeric materials.

21. A bonded composite as in claim 14 wherein at least one of said first and said second flexible sheet materials comprises a fibrous web having a multiplicity of randomly-spaced small openings extending from one of the respective major surfaces into the interior of the respective web.

22. A bonded composite as in claim 14 wherein ones of said second sub-array of bond elements extend from loci proximate the side edges to loci proximate the longitudinal axis.

23. A bonded composite, comprising:
(a) a first flexible shoot material having first and second opposing major surfaces, the first and second major surfaces defining a first overall area of said first flexible sheet material, and a first web interior between the first and second major surfaces, said first flexible sheet material being suitable for use in a personal care absorbent article;
(b) a second flexible sheet material having third and fourth opposing major surfaces, the third and fourth major surfaces defining a second overall area of said second flexible sheet material, and a second web interior between the third and fourth major surfaces, said second flexible sheet material being suitable for use in a personal care absorbent article, and being bonded to the first flexible sheet material by bond elements defining an elongate bond pattern, the elongate bond pattern having regularly repeating bond segments along a length thereof, the bond elements in each bond segment being spaced from each other according to a pattern of bond elements common to the respective bond segments, the bond pattern having a pattern length, and first and second side edges, the pattern length and the side edges, in combination, defining a third area within which the bond pattern is defined, the third area being smaller than at least one of the first and second areas of the respective first and second flexible sheet materials such that a portion of at least one of the first and second areas of respective said first and second flexible sheet materials is outside the bond pattern, the bond pattern having a bond pattern interior between the first and second side edges, and a pattern width between the first and second side edges, and a central longitudinal axis, the bond pattern comprising an array of separate and distinct elongate bond elements in a repeating arrangement affixing said first and second flexible sheet materials to each other, a bond width being defined by the width of the pattern perpendicular to the longitudinal axis, including spaces between bond elements, at any point along the length of the pattern, such bond width extending along the pattern width, bond element contact lengths being correspondingly defined along the bond width, the composite of the bond element contact lengths along a respective bond width defining a composite contact length for the respective bond width, the composite contact length, taken at equally spaced intervals along the length of the bond pattern, defining an average composite contact length, a steady power distribution across the width of the bond pattern, as the bond pattern is being formed, defining minimum variations in composite contact lengths as compared to the average composite contact length for the bond pattern for at least a complete circumferential rotation of a rotary anvil reflecting the bond pattern, wherein variations in composite contact lengths of the bond pattern reflect no more than about 13 percent of the average composite contact length of the bond pattern throughout the complete circumferential anvil rotation.

24. A bonded composite as in claim 23, the composite contact length, at any point along the length of the patter varying from the average composite contact length by no more than about 10 percent.

25. A bonded composite as in claim 23, said bond pattern comprising
(i) as first ones of said bond elements, a first sub-array of longitudinally-oriented separate, distinct, and spaced bond elements disposed along the length of the bond pattern, proximate the side edges of the bond pattern, and
(ii) as second ones of said bond elements, a second sub-array of longitudinally-oriented separate, distinct, and spaced bond elements disposed along the length of the bond pattern, inwardly of the side edges of the bond pattern and generally inwardly of said first sub-array of bond elements, respective ones of said second sub-array of bond elements having spaced first and second ends, and legs extending from the respective ends toward each other and outwardly of the longitudinal axis along the length of the bond pattern to outwardly-disposed portions of said legs between said ones of said first sub-array of bond elements.

26. A bonded composite as in claim 25, ones of said first sub-array of bond elements alternating along the length, and on opposing side edges, of the bond pattern, an imaginary contact line spanning the width of the bond pattern at a given locus along the length of the bond pattern which intersects a bond element of said first subway of bond elements on a given side of the bond pattern, also including on the opposing side of the bond pattern, a said outwardly-disposed portion of a respective said leg of the corresponding bond element of said second sub-array of bond elements, such that the distance between distal ends of the most remote ones of the bond elements along the respective imaginary contact line spanning the width of the bond pattern represents at least about 70 percent, up to 100 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

27. A bonded composite as in claim 25, ones of said first sub-array of bond elements alternating along the length, and an opposing side edges, of the bond pattern, an imaginary contact line spanning the width of the bond pattern at a given locus along the length of the bond pattern which intersects a bond element of said first sub-array of bond elements on a given side of the bond pattern, also including on the opposing side of the bond pattern, a said outwardly-disposed portion of a respective said leg of the corresponding bond element of said second sub-array of bond elements, such that the distance between distal ends of the most remote ones of the bond elements along the respective imaginary contact line spanning the width of the bond pattern represents at least about 75 percent up to 90 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

28. A bonded composite as in claim 23 wherein ones of said second sub-array of bond elements extend from loci proximate the side edges to loci proximate the longitudinal axis.

29. An absorbent article having a front portion and a rear portion, and a crotch portion extending between said front portion and said rear portion, said absorbent article comprising:
(a) a first flexible shoat material having first and second opposing major surface, the first and second major surfaces defining a first overall area of said first flexible sheet material , and a first web interior between the first and second major surfaces;
(b) a second flexible sheet material having third and fourth opposing major surfaces, the third and fourth major surfaces defining a second overall area of said second flexible sheet material, and a second web interior between the third and fourth major surfaces; and
(c) a multiplicity of bond elements defining bonds bonding said first and second flexible sheet materials to each other in a bond pattern, and
(d) an absorbent core disposed adjacent at least one of said first and said second flexible sheet materials, the bond pattern having a pattern length and including a central longitudinal axis, and first and second side edges, the pattern length and the side edges, in combination, defining a third area within which the bond pattern is formed, the third area being smaller than at least one of the first and second areas of the respective first and second flexible sheet materials such that a portion of at least one of the first and second areas of respective said first and second flexible sheet materials is outside the bond pattern, the bond pattern having a bond pattern interior between the first and second side edges, and a pattern width between the first and second side edges, the bond pattern comprising an array of separate, distinct, and spaced elongate bond elements in a repeating arrangement affixing said first and second flexible sheet materials to each other, ones of said bond elements extending across the width of said bond pattern, from loci proximate the side edges, at angles of between about 10 degrees and about 65 degrees with respect to the longitudinal axis, a bond width being defined across the width of the bond pattern perpendicular to the longitudinal axis, including spaces between bond elements, at any point along the length of the pattern, such bond width extending along the pattern width, bond element contact lengths being correspondingly defined along the bond width, the composite of the bond element contact lengths along a respective bond width defining a composite contact length for the respective bond width, the composite contact length, taken at equally spaced intervals along the length of the bond pattern, defining an average composite contact length, the composite contact length at a given point along the length of the pattern varying from the average composite contact length by no more than about 13 percent.

30. An absorbent article as in claim 29, the composite contact length, at any point along the length of the pin, varying from the average composite contact length by no more than about 10 percent.

31. An absorbent article as in claim 39, the composite contact length at any point along the length of the pattern, varying from the average composite contact length by no more than about 8 percent.

32. An absorbent article as in claim 29, said bond pattern comprising
(i) a first sub-array of longitudinally-oriented separate, distinct and spaced bond elements disposed along the length of the bond pattern, proximate the side edges of the bond pattern, and
(ii) a second sub-array of longitudinally-oriented separate, distinct, and spaced bond elements disposed along the length of the bond pattern, inwardly of the side edges of the bond pattern and generally inwardly of said first sub-array of bond elements, respective ones of said second sub-array of bond elements having spaced first and second ends, and legs extending from the respective ends toward each other and outwardly of the longitudinal axis along the length of the bond pattern to outwardly-disposed portions of said logs between said ones of said first sub-array of bond elements.

33. An absorbent article as in claim 32, said first sub-array of bond elements alternating along the length, and on opposing side edges, of the bond pattern, an imaginary contact line spanning the width of the bond pattern at a given locus along the length of the bond pattern which intersects a bond element of said first sub-array of bond elements on a given side of the bond pattern, also including on the opposing side of the bond pattern, a said outwardly-disposed portion of a respective said log of the corresponding one of said second sub-array of bond elements, such that the distance between distal ends of the most remote ones of the bond elements along the respective imaginary contact line spanning the width of the bond pattern represents at least about 70 percent, up to 100 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

34. An absorbent article as in claim 32, said first sub-array of bond elements alternating along the length, and on opposing side edges, of the bond pattern, an imaginary contact line spanning the width of the bond pattern at a given locus along the length of the bond pattern which intersects a said bond element of said first sub-array of bond elements on a given side of the bond pattern, also including on the opposing side of the bond pattern, a said outwardly-disposed portion of a respective said leg of the corresponding one of said second sub-array of bond elements, such that the distance between distal ends of the most remote ones of the bond elements along the respective imaginary contact line spanning the width of the bond pattern represents at least about 75 percent, up to 90 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

35. An absorbent article as in claim 32, said first sub-array of band elements alternating along the length, and on opposing side edges, of the bond pattern, an imaginary contact line spanning the width of the bond pattern at a given locus along the length of the bond pattern which intersects a bond element of said first sub-array of bond elements on a given side of the bond pattern, also including on the opposing side of the bond pattern, a said outwardly-disposed portion of a respective said log of the corresponding one of said second sub-array of bond elements, such that the distance between distal ends of the most remote ones of the bond elements along the respective imaginary contact line spanning the width of the bond pattern represents at least about 80 percent, up to 85 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

36. An absorbent article as in claim 29 wherein bonds corresponding to said bond elements awe formed by application of thermal energy to at least one of said first and second flexible sheet materials.

37. An absorbent article as in claim 29 wherein bonds corresponding to said bond elements are formed by application of ultrasonic-frequency energy to at least one of said first and second flexible sheet materials.

38. An absorbent article as in claim 29 wherein at least one of said first and said second flexible sheet materials comprises a fibrous web having a multiplicity of randomly-spaced small openings extending from one of the respective major surfaces into the interior of the respective web.

39. An absorbent article as in claim 29 wherein said first flexible sheet material comprises an outer cover, wherein said second flexible sheet material comprises a body side liner, and wherein at least one of said outer cover and said body side liner comprises polymeric material selected from the group consisting of polyolefins, polyesters, and polyamides, and mixtures, copolymers, and blends of said polymeric materials.

40. An absorbent article as in claim 29 wherein said second flexible sheet material comprises a body side liner and wherein said body side liner comprises material selected from the group consisting of porous foams, reticulated foams, apertured polymeric films, polymeric fibers, and natural fibers.

41. An absorbent article as in claim 39 wherein said body side liner comprises one or more of a mixture of materials selected from the group consisting of porous foams, reticulated foams, apertured polymeric films, polymeric fibers, and natural fibers.

42. An absorbent article as in claim 29, the length of said bond pattern extending from the front portion of said absorbent article to the rear portion of said absorbent article.

43. An absorbent article as in claim 29 wherein the crotch portion of said absorbent article is devoid of said bond pattern.

44. An absorbent article as in claim 29, the width of said bond pattern between the first and second side edges being about 4 millimeters to about 20 millimeters.

45. An absorbent article as in claim 29, the width of said bond pattern between the first and second side edges being about 5 millimeters to about 14 millimeters.

46. An absorbent article as in claim 29 wherein said absorbent article comprises a feminine hygiene article.

47. An absorbent article as in claim 29 wherein said absorbent article comprises a diaper.

48. An absorbent article as in claim 29 wherein said absorbent article comprises an adult incontinence product.

49. An absorbent article as in claim 29 wherein ones of said second sub-array of bond elements extend from loci proximate the side edges to loci proximate the longitudinal axis.

50. An absorbent article as in claim 29 wherein increases and decreases in power distribution across the width of the bond pattern, as the bond pattern is being formed, can be defined by variations in composite contact lengths as compared to the average composite contact length for a given bond pattern for at least a complete circumferential rotation of a rotary anvil, wherein variations in composite contact lengths of the bond pattern reflect no more than about 13% of the average composite contact length of the bond pattern throughout the complete circumferential anvil rotation.

51. An absorbent article having a front portion and a rear portion, and a crotch portion extending between said front portion and said rear portion, said absorbent article comprising:

(a) a first flexible sheet material having first and second opposing major surfaces, the first and second major surfaces defining a first overall area of said first flexible sheet material, and a fast web interior between the first and second major surfaces;

(b) a so flexible sheet material having third and fourth opposing major surfaces, the third and fourth major surfaces defining a second overall area of said second flexible sheet material, and a second web interior between the first and second major surfaces;

(c) a multiplicity of bond elements defining bonds bonding said first and second flexible sheet materials to each other in a bond pattern, and (d) an absorbent core disposed adjacent at least one of said first and said second flexible sheet materials, the bond pattern having a pattern length and including a central longitudinal axis, and first and second side edges, the pattern length and the side edges, in combination, defining a third area within which the bond pattern is formed, the third area being smaller than at least one of the first and second areas of the respective first and second flexible sheet materials such that a portion of at least one of the first and second areas of respective said first and second flexible sheet materials is outside the bond pattern, the bond pattern having a bond pattern interior between the first and second side edges, and a pattern width between the first and second side edges, the bond pattern comprising an array of separate, distinct, and spaced elongate bond elements in a repeating arrangement affixing said first and second flexible sheet materials to each other, (e) as ones of said bond elements, a first sub-array of longitudinally-oriented separate, distinct and spaced bond elements disposed along the length of, and proximate the side edges of the bond pattern, and (f) as ones of said bond elements, a second sub-array of longitudinally-oriented separate, distinct, and spaced bond elements disposed along the length of the bond pattern, inwardly of the side edges of the bond pattern and generally inwardly of said first sub-array of bond elements, respective ones of said second sub-array of bond elements having spaced first and second ends, and legs extending from the respective first and second ends toward each other and outwardly of the longitudinal axis along the length of the bond pattern to outwardly-disposed portions of said legs between ones of said first sub-array of bond elements.

52. An absorbent article as in claim 51, said bond elements of said first sub-array of bond elements alternating along the length, and on opposing side edges, of the bond pattern, an imaginary contact line spanning the width of the bond pattern at a given locus along the length of the bond pattern which intersects a bond element of said first sub-array of bond elements on a given side of the bond pattern, also including on the opposing side of the bond pattern, a said outwardly-disposed portion of a respective said leg of the corresponding bond element of said second sub-array of bond elements, such that the distance between distal ends of the most remote ones of the bond elements along the respective imaginary contact fine spanning the width of the bond pattern represents at least about 70 percent, up to 100 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during first of the bond pattern.

53. An absorbent article as in claim 51, said bond elements of said first sub-array of bond elements alternating along the length, and on opposing side edges, of the bond patter, an imaginary contact line spanning the width of the bond pattern at a given locus along the length of the bond pattern which intersects a bond element of said first sub-array of bond elements on a given side of the bond patter also including on the opposing side of the bond pattern, a said outwardly-disposed portion of a respective said leg of the corresponding bond element of said second sub-array of bond elements, such that the distance between distal ends of the most remote ones of the bond elements along the respective imaginary contact line spanning the width of the bond pattern represents at least about 75 percent, up to 90 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

54. An absorbent article as in claim 51, said bond elements of said first sub-array of bond elements alternating along the length, and on opposing side edges, of the bond pattern, an imaginary contact line spanning the width of the bond pattern at a given locus along the length of the bond pattern which intersects a bond element of said first sub-array of bond elements on a given side of the bond pattern, also including on the opposing side of the bond pattern, a said outwardly-disposed portion of a respective said leg of the corresponding bond element of said second sub-array of bond elements, such that the distance between distal ends of the most remote ones of the bond elements along the respective imaginary contact line spanning the width of the bond pattern represents at least about 80 percent, up to 85 percent, of the width of the bond pattern, whereby the outwardly-disposed portions of the respective said legs provide balancing support on opposing sides of the longitudinal axis from respective ones of said first sub-array of bond elements or opposing ones of said second sub-array of bond elements during formation of the bond pattern.

55. An absorbent article as in claim 51 wherein bonds corresponding to said bond elements are formed by application of thermal energy to at least one of said first and second flexible sheet materials.

56. An absorbent article as in claim 51 wherein bonds corresponding to said bond elements are formed by application of ultrasonic-frequency energy to at least one of said first and second flexible sheet materials.

57. An absorbent article as in claim 51 wherein at least one of said first and said second flexible sheet materials comprises polymeric material selected from the group consisting of polyolefins, polyesters, and polyamides, and copolymers, mixtures, and blends of said polymeric materials.

58. An absorbent article as in claim 51 wherein at least one of said first and said second flexible sheet materials comprises a fibrous web having a multiplicity of randomly-spaced small openings extending from one of the respective major surfaces into the interior of the respective web.

59. An absorbent article as in claim 51 wherein ones of said second sub-array of bond elements extend from loci proximate the side edges to loci proximate the longitudinal axis.

\* \* \* \* \*